US009195237B2

(12) United States Patent
Gardner et al.

(10) Patent No.: US 9,195,237 B2
(45) Date of Patent: *Nov. 24, 2015

(54) WAVEFORM SHAPING INTERFACE

(71) Applicant: FUJIFILM Dimatix, Inc., Lebanon, NH (US)

(72) Inventors: Deane A. Gardner, Cupertino, CA (US); Paul A. Hoisington, Hanover, NH (US); Daniel Cote, Hartland, VT (US)

(73) Assignee: FUJIFILM Dimatix, Inc., Lebanon, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/269,403

(22) Filed: May 5, 2014

(65) Prior Publication Data

US 2014/0244052 A1 Aug. 28, 2014

Related U.S. Application Data

(63) Continuation of application No. 11/532,473, filed on Sep. 15, 2006, now Pat. No. 8,740,334.

(60) Provisional application No. 60/717,784, filed on Sep. 15, 2005.

(51) Int. Cl.
*B41J 29/38* (2006.01)
*G05D 7/06* (2006.01)
(Continued)

(52) U.S. Cl.
CPC ............ *G05D 7/0629* (2013.01); *B41J 2/0456* (2013.01); *B41J 2/04561* (2013.01);
(Continued)

(58) Field of Classification Search
USPC .................. 347/5, 9, 10, 14, 19, 12
See application file for complete search history.

(56) References Cited

U.S. PATENT DOCUMENTS 5,265,315 A 11/1993 Hoisington et al.
5,914,732 A 6/1999 Sakai et al.
(Continued)

FOREIGN PATENT DOCUMENTS

JP H5-149769 6/1993
JP 2001-277487 9/2001
(Continued)

OTHER PUBLICATIONS

International Search Report and Written Opinion dated Feb. 14, 2007 from corresponding international application No. PCT/US2006/036275, 13 pages.
(Continued)

*Primary Examiner* — Lam Nguyen
(74) *Attorney, Agent, or Firm* — Fish & Richardson P.C.

(57) ABSTRACT

A method and system of facilitating development of fluids having a variety of elemental compositions are disclosed. A graphical user interface allows user interaction with a lab deposition system to control fluid drop ejection of fluids through multiple nozzles. Fluid drop ejection and drop formation can vary from fluid to fluid, and require adjustments to waveform parameters of a drive pulse applied to the multiple nozzles. The system implements a drop watcher camera system to capture real-time still and video images of fluid drops as they exit the multiple nozzles. The captured drop formation of the fluid drops are displayed to the user, and based on the images the waveform parameters are adjusted and customized specific for individual fluid. In addition to adjusting the drive pulse that effects fluid drop ejection, a tickle pulse can also be adjusted and customize to prevent clogging of the nozzles.

23 Claims, 17 Drawing Sheets

(51) Int. Cl.
  *B41J 2/045* (2006.01)
  *B41J 2/21* (2006.01)
  *B41J 29/393* (2006.01)
  *G01N 35/10* (2006.01)
  *B01L 3/02* (2006.01)

(52) U.S. Cl.
  CPC ......... *B41J 2/04586* (2013.01); *B41J 2/04588* (2013.01); *B41J 2/2142* (2013.01); *B41J 29/393* (2013.01); *G01N 35/1016* (2013.01); *B01L 3/0268* (2013.01)

(56) References Cited

U.S. PATENT DOCUMENTS

| | | | |
|---|---|---|---|
| 6,094,280 | A | 7/2000 | Hayasaki et al. |
| 6,890,062 | B2 | 5/2005 | Bell et al. |
| 2003/0090534 | A1 | 5/2003 | Valero et al. |
| 2004/0085384 | A1 | 5/2004 | Ju et al. |
| 2004/0130585 | A1 | 7/2004 | Weksler et al. |
| 2005/0041073 | A1 | 2/2005 | Fontaine et al. |
| 2005/0270318 | A1 | 12/2005 | Noda |
| 2006/0033768 | A1 | 2/2006 | Uraki et al. |

FOREIGN PATENT DOCUMENTS

| | | |
|---|---|---|
| JP | 2002-356248 | 10/2002 |
| JP | 2003-28696 | 1/2003 |
| JP | 2004-361234 | 12/2004 |
| JP | 2005-21755 | 1/2005 |
| JP | 2005-22211 | 1/2005 |
| JP | 2005-41025 | 2/2005 |
| JP | 2005-201895 | 7/2005 |

OTHER PUBLICATIONS

International Preliminary Report on Patentability dated Mar. 27, 2008 from corresponding international application No. PCT/US2006/036275, 7 pages.
First Office action dated Mar. 25, 2010 received in corresponding Chinese application No. 200680042737.3, 4 pages.
First Office action received in co-pending Japanese application No. 2008-531407 dated Jul. 19, 2011, 7 pgs.
Second Office action received in co-pending Japanese application No. 2008-531407 dated Feb. 21, 2012, 4 pgs.
Reexamination Report in Japanese Application No. 2008-531407, dated Oct. 9, 2012, 8 pages.
Japanese Office Action in Japanese Application No. 2008-531407 (Appeal No. 2012-011551), issued Mar. 12, 2013, 7 pages.
Office Action for KR Application No. 10-2008-7008678 dated Apr. 23, 2013 with English translation.

WAVEFORM SHAPING INTERFACE

CLAIM OF PRIORITY

This application is a continuation of and claims priority under 35 U.S.C. §120 to U.S. application Ser. No. 11/532,473, filed on Sep. 15, 2006, which claims the benefit of the filing date of U.S. Patent Application No. 60/717,784, filed on Sep. 15, 2005. The contents of both of which are incorporated by reference as part of this application.

BACKGROUND

The following disclosure is directed to systems that use ejection of fluid droplets.

In various industries it is useful to deposit a fluid in a controllable manner onto a substrate by ejecting droplets of the fluid from a fluid ejection module. For example, ink jet printing uses a printhead to produce droplets of ink that are deposited on a substrate, such as paper or transparent film, in response to an electronic digital signal, to form an image on the substrate.

An ink jet printer typically includes an ink path from an ink supply to a printhead that includes nozzles from which ink drops are ejected. Ink drop ejection can be controlled by pressurizing ink in the ink path with an actuator, such as, for example, a piezoelectric deflector, a thermal bubble jet generator, or an electrostatically deflected element. A typical printhead has a line of nozzles with a corresponding array of ink paths and associated actuators, and drop ejection from each nozzle can be independently controlled. In a so-called "drop-on-demand" printhead, each actuator is fired to selectively eject a drop at a specific pixel location of an image, as the printhead and a printing media are moved relative to one another. A high performance printhead may have several hundred nozzles, and the nozzles may have a diameter of 50 microns or less (e.g., 25 microns), may be separated at a pitch of 100-300 nozzles per inch, and may provide drop sizes of approximately 1 to 70 picoliters (pl) or less. Drop ejection frequency is typically 10 kHz or more.

A printhead can include a semiconductor body and a piezoelectric actuator, for example, the printhead described in Hoisington et al., U.S. Pat. No. 5,265,315. The printhead body can be made of silicon, which is etched to define ink chambers. Nozzles can be defined by a separate nozzle plate that is attached to the silicon body. The piezoelectric actuator can have a layer of piezoelectric material that changes geometry, or bends, in response to an applied voltage. The bending of the piezoelectric layer pressurizes ink in a pumping chamber that communicates with a nozzle, and an ink drop is formed.

Fluid drop formation typically is altered by adjusting the waveform parameters such as voltage amplitude, duration of the voltage pulse, slope of the waveform, number of pulses, and other adjustable parameters of the drive pulse delivered to the piezoelectric actuator. The optimal waveform parameters for different fluids vary depending on a particular fluid's physical properties. Typically, the optimal waveform parameters for a specific fluid are determined empirically.

SUMMARY

The methods, apparatus, and system described here implement techniques for facilitating deposition of fluids of various compositions in a lab deposition system. Specifically, an interactive user interface coupled to a waveform editor facilitates real-time adjustments of waveforms customized for fluids having various compositions.

In general, in one aspect, the techniques can be implemented in as system that includes a lab deposition system; a waveform editor for facilitating adjustments of various waveform parameters; a user interface to allow interactive adjustments of the waveform parameters; and a camera system in communication with the waveform editor to provide real-time visual feedback of the fluid drop corresponding to the adjustments made by the user.

The techniques also can be implemented to include one or more of the following features of the user interface. A select pattern window can be implemented to select and load a print pattern from a list of predetermined print patterns. The select pattern window can also be implemented to create custom print patterns. A load/unload substrate window can be implemented to facilitate loading and unloading of a substrate onto a platen of the lab deposition system. A print set-up window can be implemented to print the selected print pattern by initiating fluid drop ejection. A cartridge settings window can be implemented to select a predetermined waveform stored in a file list and adjust the voltage level of the selected waveform for each nozzle. The cartridge settings window can also be implemented to enable a tickle control to prevent fluid from drying and clogging the nozzles. The cartridge settings window can additionally be implemented to adjust a temperature of a cartridge holding the fluid and a meniscus vacuum setting. The cartridge settings window can further be implemented to set the clean cycle for maintaining proper operation of the nozzles. A waveform editor window can be implemented to facilitate the adjustment of various waveform parameters. A drop watcher window can be implemented to visually inspect fluid drops in real-time.

The techniques can also be implemented to include one or more of the following features of the waveform editor. Multiple waveform parameters can be adjusted through an user interface presented on the waveform editor window. The adjustable waveform parameters can include voltage level, slew rate, duration, number of segments, frequency, and width of the drive pulse applied to the printhead. The parameters are adjustable for each nozzle, independent of the parameters of other nozzles. In addition, the parameters can be adjusted for a jetting waveform and a non jetting waveform. The jetting waveform is the drive pulse applied to effect fluid drop ejection from the nozzles. The non-jetting waveform is the drive pulse applied to prevent clogging of the nozzles without effecting fluid drop ejection.

The techniques can further be implemented to include one or more of the following features of the drop watcher system. A camera can be placed near the printhead to capture video and still images of the fluid drop characteristics for each fluid type. The drop characteristics assessed can at least include size and shape of the drop in addition to the drop speed. The drop watcher system can be implemented in conjunction with the user interface to couple with the waveform editor. The results of the adjustments to the waveform parameters can be immediately seen on a display displaying the video and still images of fluid drops ejecting from each nozzle. Depending on the fluid drop characteristics captured through the drop watcher system, the waveform parameters can be adjusted appropriately in real-time.

The techniques can be implemented to realize one or more of the following advantages. The waveform editor in combination with the drop watch camera system may enable real-time waveform editing, and thus speed up discovery or development of new liquids with variety of compositions and characteristics. Further, fluids can be tested using a droplet ejection system suitable for small volumes of liquid, permitting valuable test liquids to be conserved, and thus reducing the costs of testing.

The details of one or more embodiments are set forth in the accompanying drawings and the description below. Other features and advantages will be apparent from the description and drawings, and from the claims.

BRIEF DESCRIPTION OF DRAWINGS

Like reference symbols in the various drawings indicate like elements.

DETAILED DESCRIPTION

As discussed above, a tremendous variety of liquids with different material compositions are available, and the number of such liquids continues to increase as new materials and compositions are investigated. Liquids may need to be tested for their effectiveness in a proposed application, and droplet ejection conditions may need to be individually determined for optimal deposition of a particular liquid.

A typical liquid that may need to be tested is ink, and for illustrative purposes, the techniques and droplet ejection modules are described below in reference to a printhead module that uses ink as the liquid. However, it should be understood that other liquids can be used, such as electroluminescent or liquid crystal material used in the manufacture of displays, metal, semiconductor or organic materials used in circuit fabrication, e.g., integrated circuit or circuit board fabrication, and organic, biological, or bioactive materials, e.g., for drugs or the like.

For example, bioactive materials, such as protein and DNA can be expensive and fragile, requiring special handling techniques. Ink jet technology with non-contact printing process is ideal to provide careful, accurate, and speedy deposition of the bioactive materials in minute drops to not only minimize costs but to speed up reaction processes. A disposable reaction well with hundreds or more of distinct reaction sites can be fabricated as a substrate to facilitate completion of increasingly higher number of diagnostic tests that could be conducted in parallel. In addition, deposition of bioactive molecules can allow known materials to be applied to substrates in large quantity of molecules to fabricate those molecules in situ using non-contact ink-jet deposition of precursor materials. Oligomeric materials (polymers consisting of two to four monomers) such as DNA and peptides are ideal candidates for ink-jet deposition because DNA and peptides are synthesized using combinatorial synthesis.

Figure 1:
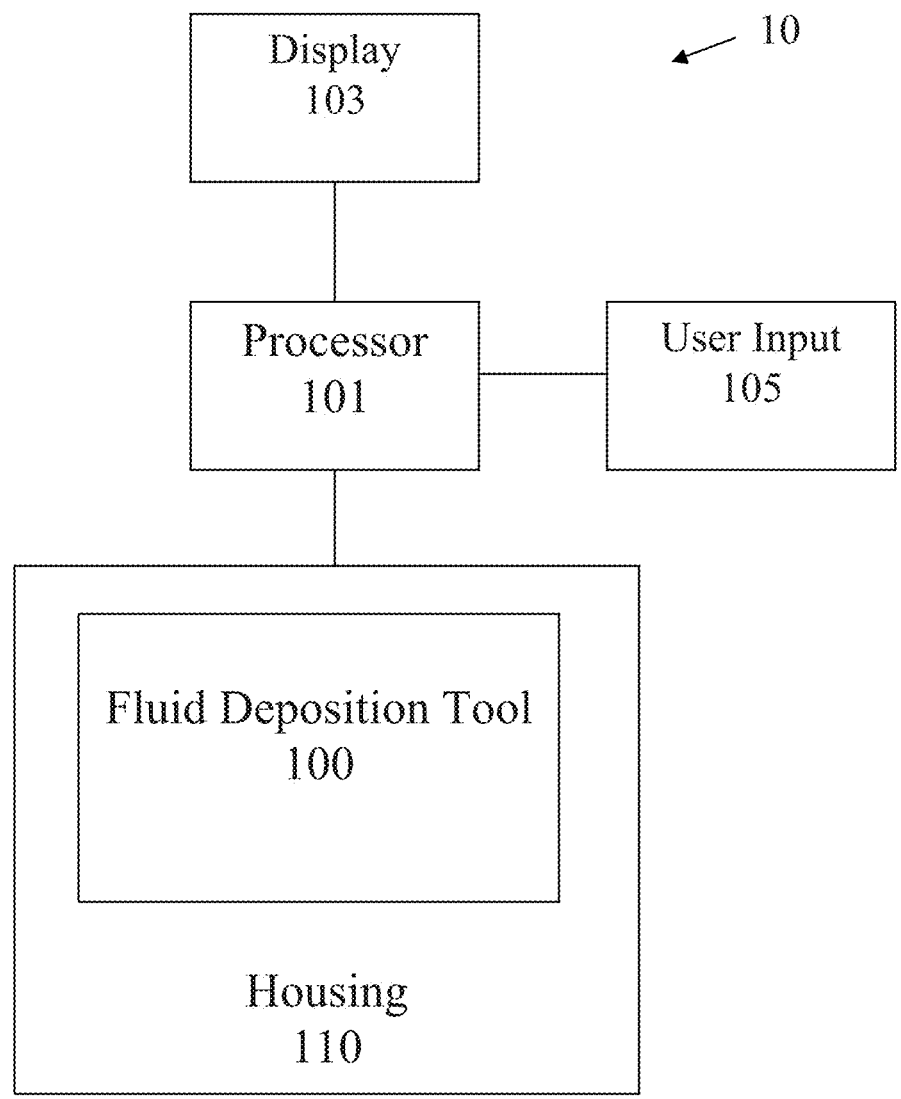
FIG. 1 is a block diagram of a lab deposition system.

A lab deposition system 10 can be substantially as represented in FIGS. 1-4. Referring to FIG. 1, a block diagram representation of a lab deposition system 10 comprising a fluid deposition device 100 within a housing 110 is shown. In this implementation, the fluid deposition device 100 is coupled to a processor 101. The processor 101 can be connected to a display 103 (e.g., a monitor) and a user input device 105 (e.g., a keyboard and/or mouse). The processor 101 can provide instructions to various components of the fluid deposition device 100, as shall be described further below. The display 103 and user input device 105 can allow a user to input operation parameters and make adjustments to a fluid deposition process, as well as view feedback provided by the processor 101, as described further below.

Figure 2:
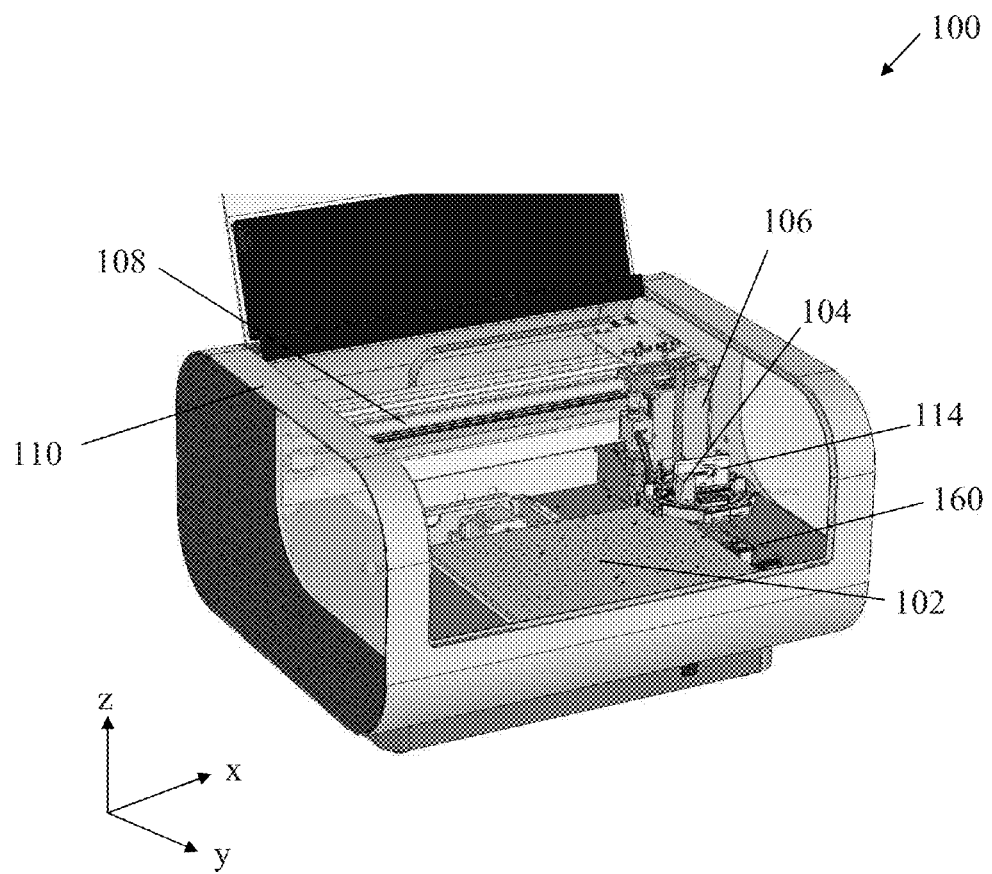
FIG. 2 shows a fluid deposition device including a drop watcher camera system.

Referring to FIG. 2, one embodiment of the fluid deposition device 100 is shown. The fluid deposition device 100 includes a platen 102 configured to support a substrate during a print operation. A cartridge mount assembly 104 is attached to a frame 106 and positioned above the platen 102. The cartridge mount assembly 104 can translate along a rail 108 in the y-direction, providing movement relative to a substrate positioned on the platen 102. Additionally, the cartridge mount assembly 104 can move upward and downward relative to the platen 102, i.e., in the z-direction, to provide relative vertical movement between a print cartridge mounted therein and the substrate.

In addition, a drop watcher camera system 160 can be mounted to one side of the platen 102. The camera system 160 allows a user to watch fluid drops as they exit the print cartridge 114 and are printed on a substrate positioned in front of the camera system 160. By strobing a light slightly out of phase with the nozzle firing, a series of pictures of a series of fluid drops in flight between the nozzle and the substrate can be obtained. A composite of the series of pictures viewed together can give the illusion of a video clip of a single drop being ejected from a nozzle: in reality, the "video" is actually a composite of a series of still pictures taken of many different drops at slightly different stages of formation and flight. The strobed images can be averaged together to obtain a resultant image or alternatively, each individual image frame can be analyzed to obtain various drop characteristics.

In some implementations, a high speed video camera is implemented to capture real time video images of the fluid drops being ejected thought one or more nozzles in the print cartridge 114. A high speed video camera can be equipped with a charge-couple device (CCD), complementary-symmetry/metal-oxide semiconductor (CMOS) or other suitable image sensors. A CCD camera can capture images at speeds of up to 1000 frames per second, and this can be increased to 1,000,000 frames per second by adding an image intensifier. An image intensifier is a device that amplifies visible and near-infrared light from an image to facilitate a dimly lit scene to be viewed by a camera. A CMOS sensor can be more cost effective than a CCD sensor and easier to integrate with on-chip memory and processing functions. A CMOS sensor can capture images at speeds of up to 1000 frames per second. Other image sensors capable of similar or higher frame rates can be implemented. The real time video images of the fluid drops can be used to capture various drop characteristics of the fluid drops in various stages of formation and flight. The drop characteristics can be analyzed to provide feedback information to adjust the waveform characteristics of the drive pulse delivered to the print head The adjustments can be performed automatically or manually by a user.

The display 103 can be used to provide a graphical display to the user of the drops as captured by the camera system 160. Simultaneously, for example, using a split screen or multiple frames within a screen, a graphical representation of a waveform corresponding to the drive pulse to an actuator included in the print cartridge 114 to fire the nozzles can be displayed. The user can view the fluid drops and waveform and make adjustments as desired using the user input device 105. For example, the user can adjust the drive voltage delivered to the printhead within the print cartridge 114, duration of the voltage pulse, slope of the waveform, number of pulses, and other adjustable parameters. The user input is used by the processor 101, e.g., by a software application executing in the processor 101, to adjust the signals sent to the actuator or actuators located within the print cartridge 114.

Figure 3:
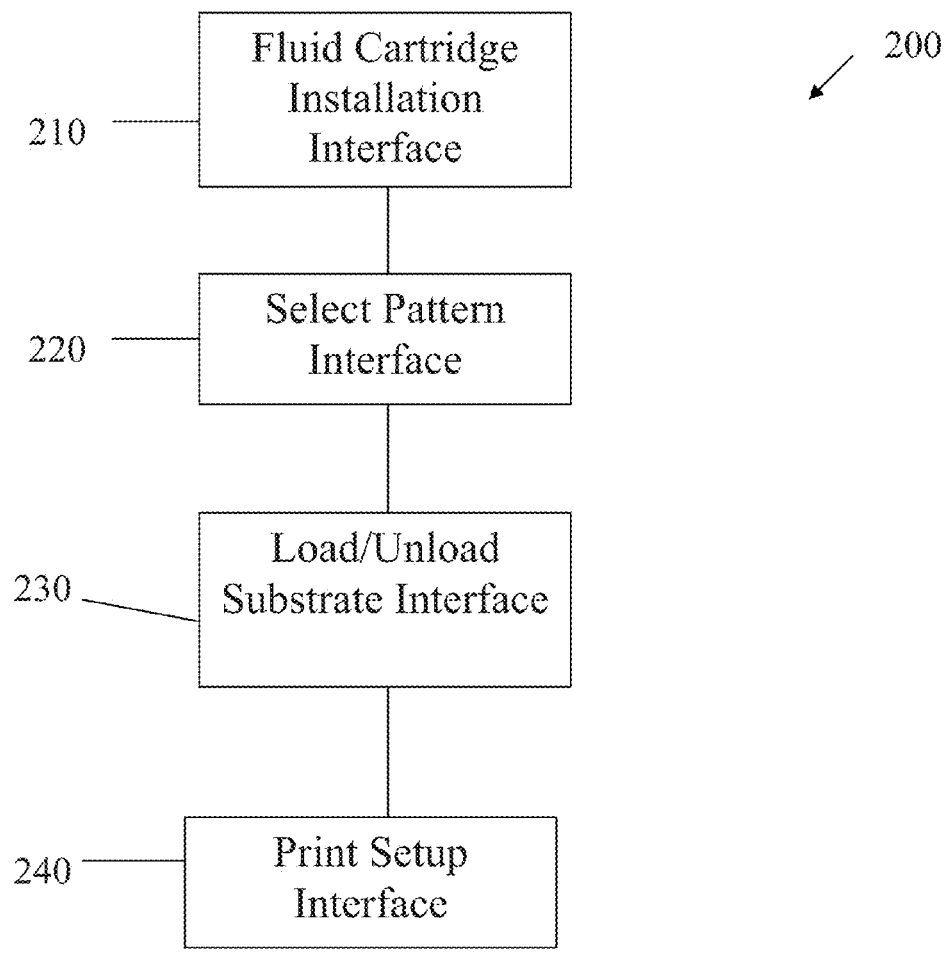
FIG. 3 is a block diagram of a graphical user interface.

In addition, the software application can include a graphical user interface (GUI) 200 comprising multiple interfaces corresponding to one or more lab deposition system functions. FIG. 3 is a block diagram representing one implementation of the GUI 200. A fluid cartridge installation interface 210 can be implemented to facilitate the physical installation of the fluid cartridge by the user. A select pattern interface 220 can be implemented to facilitate user selection of a print pattern from a stored list of predetermined print patterns. The predetermined print patterns can be used to perform test printing of individual fluids on a substrate. A load/unload substrate interface 230 can be implemented to facilitate loading and unloading of the substrate onto the platen 102. The load/unload substrate interface can also be used to facilitate adjustments of temperature and vacuum settings to the platen 102. The vacuum acts to hold the substrate firmly onto the platen during jetting of the fluid, and the temperature adjustment to the platen facilitates creation of an environment appropriate to temperature sensitive fluids. Jetting of the fluid will not occur until the temperature of the platen reaches the adjusted temperature value. The load/unload substrate interface can further be implemented to facilitate adjustments of the thickness of the substrate. Depending on the thickness of the substrate entered by the user, the cartridge height is automatically adjusted by the lab deposition system 10. A print setup interface 240 can be implemented to facilitate the selection of cartridge settings. Once the cartridge setting is selected by the user, the jetting process can be initiated based on the selected print pattern, substrate settings, and the cartridge settings.

Figure 4:
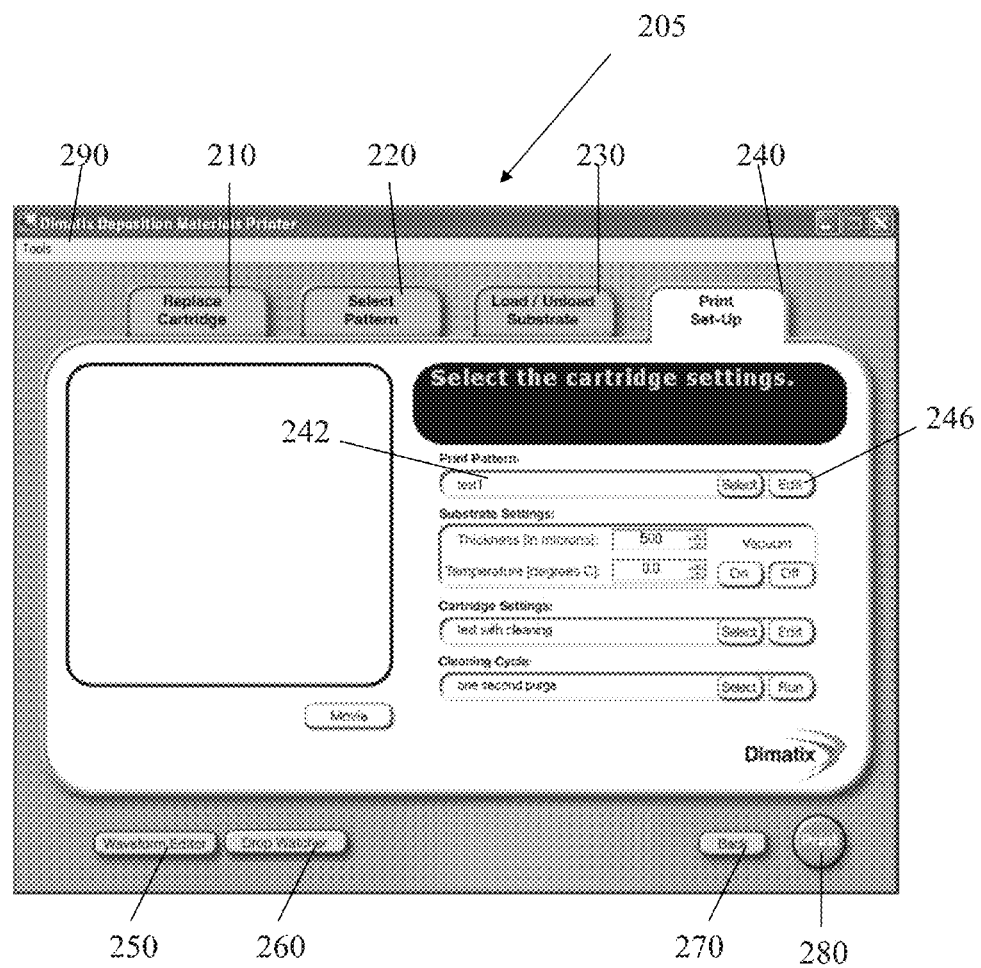
FIG. 4 is a representative screenshot of a Print Set-Up interface.

Jetting of a fluid having specific composition and fluid characteristics requires customization of the cartridge settings. FIG. 4 is a screenshot of one implementation of the GUI 200 comprising an interface window 205 including multiple interfaces accessible through user selection of well known GUI tabs (210, 220, 230, and 240), buttons (250, 260, 270, and 280), and menu buttons 290. In alternate implementations, other GUI components in addition to or in place of the GUI tabs (210, 220, 230, and 240), buttons (250, 260, 270, and 280), and menu button 290 can be used. In the implementation represented in FIG. 4, the user can select an edit button 246 placed next to a cartridge settings selection window 242 to launch a cartridge settings editor 300 as shown in FIG. 5.

Figure 5:
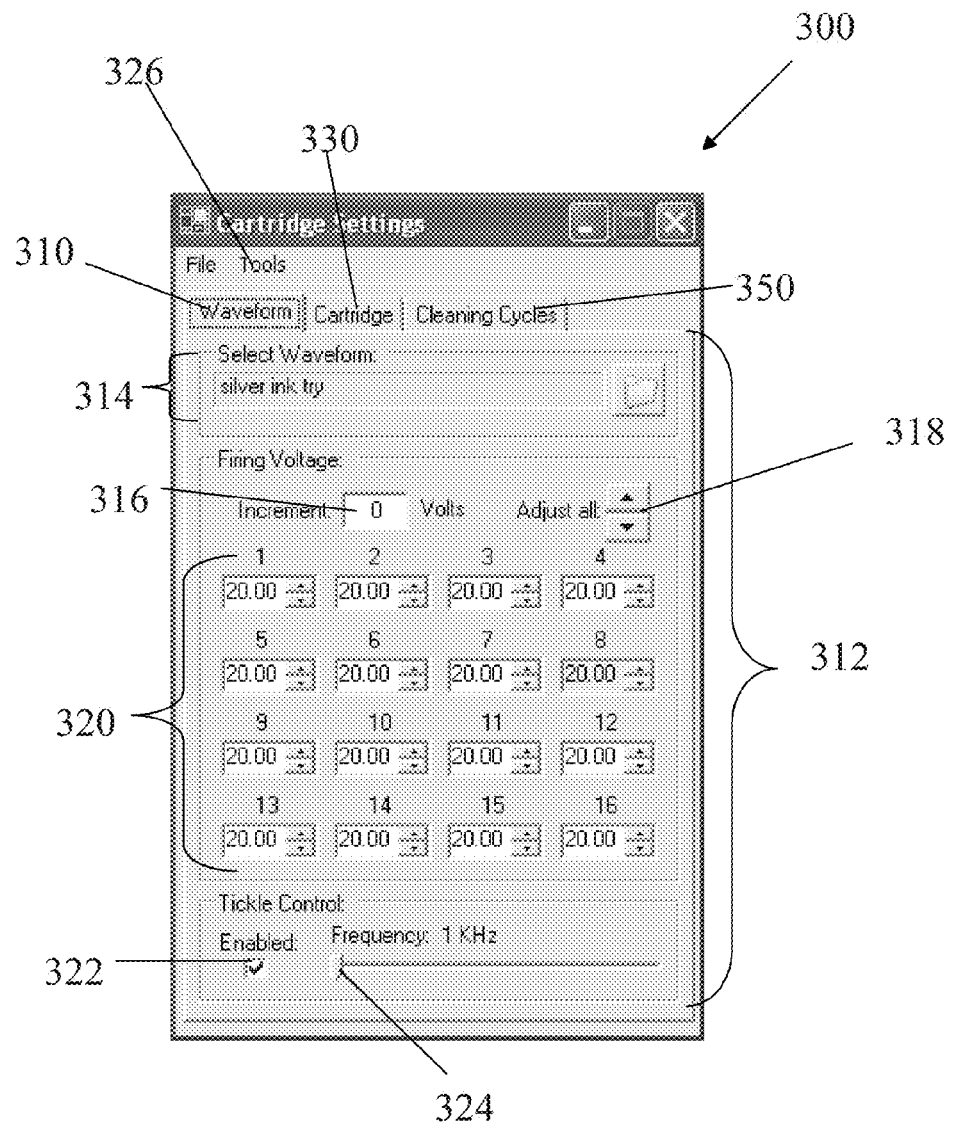
FIG. 5 is a representative screenshot of a Cartridge Settings interface.

FIG. 5 represents a screenshot of one implementation of the cartridge settings editor 300. The user is presented with three GUI tabs 310, 330, and 350, each tab representing a specific editor interface. User selection of a GUI tab labeled "Waveform" 310 can be implemented to display a waveform level interface 312 to facilitate user selection of a predetermined waveform using a "File" search box 314. A list of predetermined waveforms is stored in a folder to provide template waveforms corresponding to a list of identified liquids. When jetting a new liquid of unknown fluid drop ejection characteristics, the user can start with one of the template waveforms and make necessary adjustments to the waveform as described in the following paragraph below. The waveform level interface 312 can also be implemented to adjust a voltage level for the selected waveform. The voltage level can be adjusted for all nozzles together in equal stepwise increments by allowing the user to enter a voltage increment in a voltage increment input box 316 and selecting an increase/decrease button 318. Alternately, the voltage level can be adjusted individually for each nozzle by allowing the user to enter a voltage level in multiple voltage input boxes 320, one for each nozzle. In addition, the waveform level interface 312 can be implemented to enable a Tickle Control 322 and adjust a frequency 324 of the Tickle Control.

Figure 6:
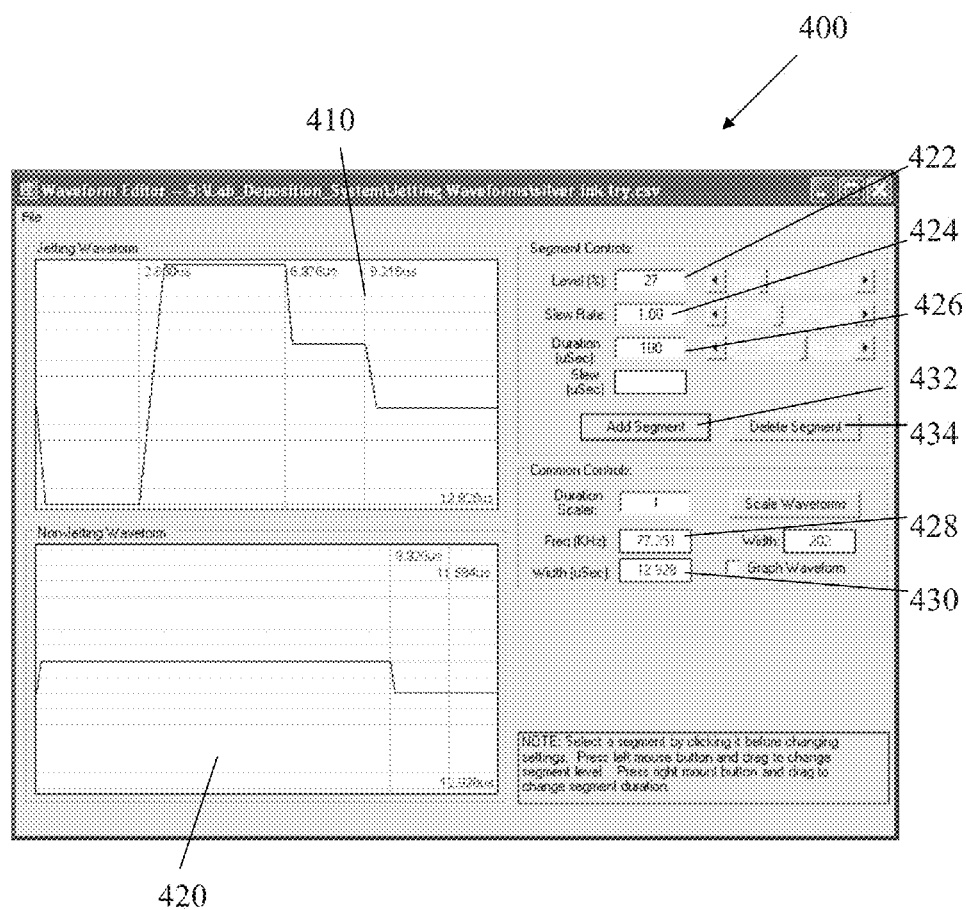
FIG. 6 is a representative screenshot of a Waveform Editor interface.

Once the voltage level has been adjusted by the user, a Waveform Editor 400 as shown in FIG. 6 allows the user to adjust additional waveform parameters. The Waveform Editor 400 can be activated and displayed to the user by a user selection of a "Tools" menu button 326 as shown in FIG. 5 or a "Waveform Editor" button 250 as shown in FIG. 4. A "Jetting Waveform" display 410 and a "Non-Jetting Waveform" display 420 are located on the left side of the Waveform Editor 400. A Jetting Waveform represents a drive pulse applied to the nozzles to effect jetting of a fluid. A Non-Jetting Waveform represents a drive pulse of a lower amplitude than the Jetting Waveform applied to the nozzles to move a meniscus of a fluid drop without effecting jetting of the fluid. Enabling the Tickle Control activates the Non-Jetting Waveform. The user can selectively adjust the waveform parameters for a specific waveform segment by selecting the specific segment of the waveform displayed on the Jetting Waveform display 410 and the Non-Jetting Waveform display 420. User selection of the segment can be performed through a mouse click. Once a segment has been selected by the user, any adjustments of % voltage level 422, slew rate 424, duration 426, slew, frequency 428, and width 430 settings are effected on the selected segment. In addition, segments can be added or deleted by selecting "Add Segment" 432 or "Delete Segment" 434 button.

Figure 7:
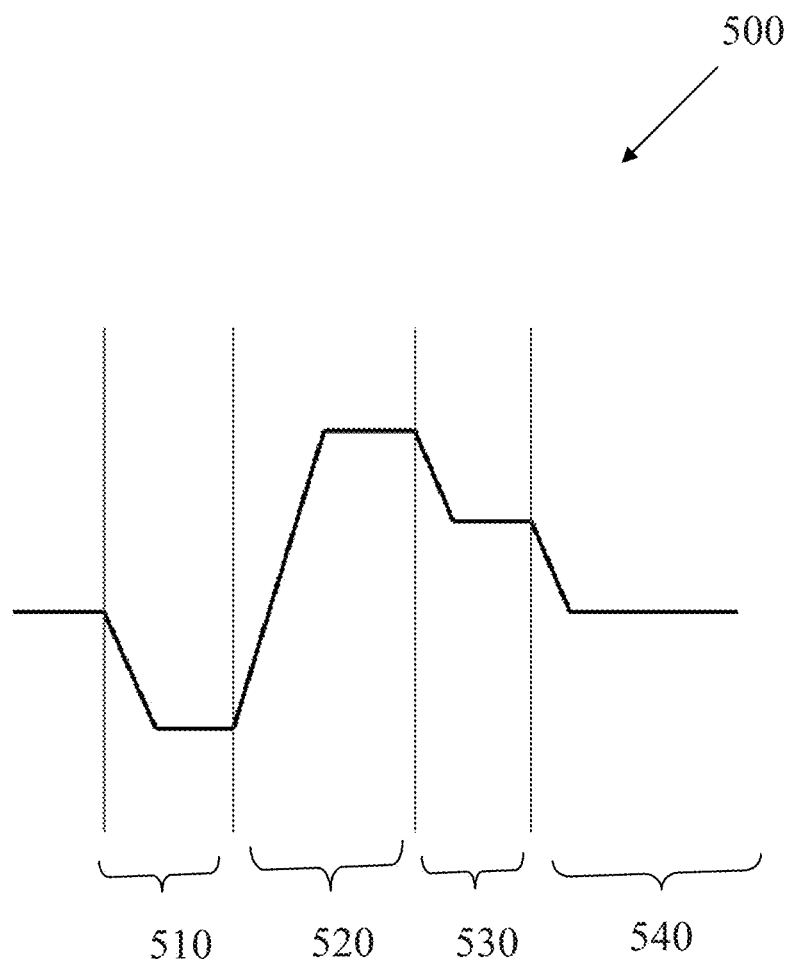
FIG. 7 is a cartoon representation of a waveform.

The waveform parameters can be adjusted to match the fluid properties of each different liquid. For a thicker liquid of higher viscosity, the voltage level of the waveform needs to be adjusted to a higher level. Likewise, a steeper slew rate, or rise time of the waveform is needed. In general, the higher viscosity fluid is less sensitive and provides for a higher frequency performance. A low viscosity fluid requires a lower voltage, a slower rise time and is more sensitive to drive pulse formation. The low viscosity fluid also does not perform as well at high frequencies. FIG. 7 represents an example waveform 500 comprising four segments 510, 520, 530, and 540. The first two segments 510 and 520 have the most significant impact on the drop velocity and formation. The basic strategy to obtain good drop velocity and good drop formation is to set the voltage to a relatively high level while visually inspecting that the drop formation is acceptable. The drop watcher camera system 160 mounted to one side of the platen 102 can be used to observe the drop formation from the nozzles. Then, based on the visual inspection of the drop formation, the first two segments 510 and 520 can be adjusted. The focus is to obtain higher drop velocities while maintaining good drop formation. Reducing the voltage can improve the drop formation, and small adjustments of the last two segments 530 and 540 can provide further improvements in drop formation.

Figure 8:
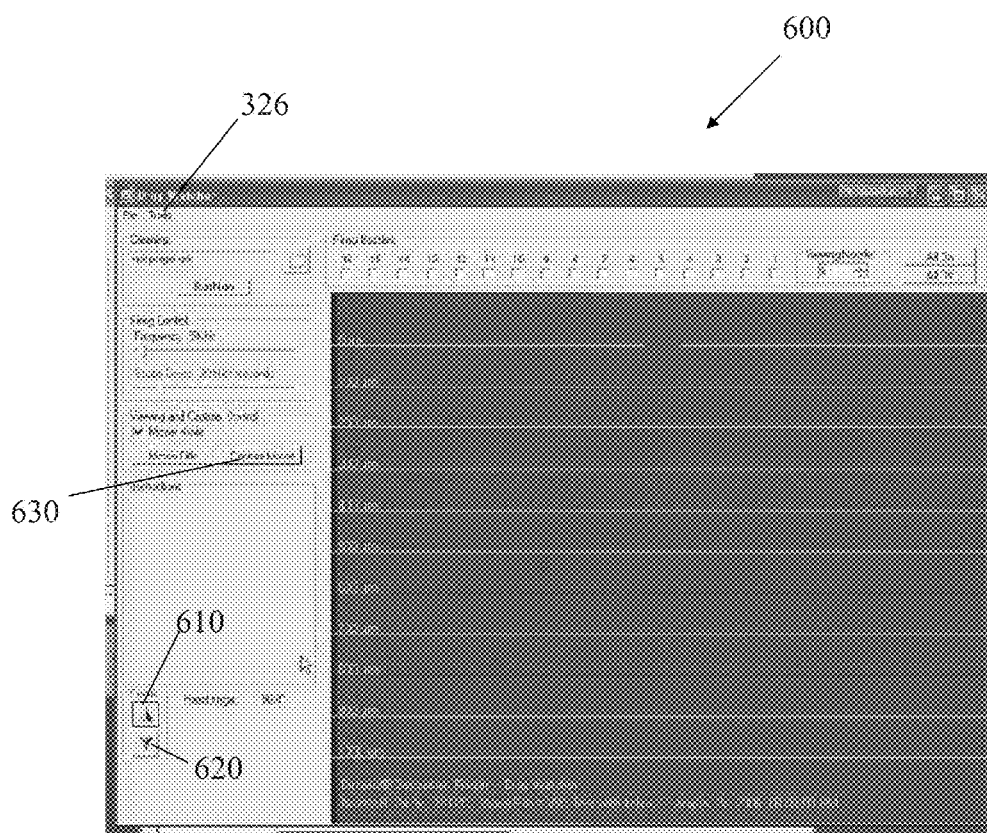
FIG. 8 is a schematic diagram of a representative Drop Watcher Viewer.

Still images and video images of drop formation captured by the drop watcher camera system 160 can be displayed to the user through a Drop Watcher Viewer 600 as shown in FIG. 8. A user selection of a "Drop Watcher" button 260 can activate the display of the Drop Watcher Viewer 600. In one embodiment, the Waveform Editor and the Drop Watcher Viewer are provided and displayed to the user simultaneously in order to facilitate the customization of a waveform specific for a given fluid. This allows the user to perform real-time adjustments to the waveform as describe above. The Drop Watcher Viewer 600 can allow the user to see the nozzles of the cartridge, the nozzle surface, and watch jetting of the fluid. The user can select each nozzle to visually inspect firing of each nozzle. A mouse click on a desired nozzle fires the nozzle or turns the nozzle off. There are also two arrow buttons (610 and 620) near the bottom left of the screen which allow you to focus the drop watcher camera system on a nozzle and drops ejected from the nozzle. Alternatively or in addition, the system can include automated or semi-automated intelligence (e.g. implemented as one or more algorithms in software and/or hardware) to control adjustment of the waveform. For example, an automated (without user input) or semi-automated (with at least some user input) algorithm could apply visual object recognition techniques to the camera output to determine properties of the drops being output by the deposition system, and then adjust the firing waveform automatically based on predetermined criteria.

The system provides the user with two different viewing modes. A mouse click on Movie Mode button 630 allows the user to watch the drops in flight as they are ejected from the nozzle. If Movie Mode is not selected the user can "freeze" the drop in flight for closer inspection and measurement. By adjusting the strobe delay, the user can freeze the drop at different positions after it leaves the nozzle. A velocity measurement can be performed by setting the strobe delay to 100 μsec while not in Movie Mode. This allows the drop to be captured 100 μsec after the fire pulse. By selecting the Graticle scale from the Tools menu button 326 on the Drop Watch Viewer, a scale is displayed on the screen electrically. The user can mouse click on the nozzle and drag it to the O line of the scale to determine the distance traveled by the drop in 100 μsec. This rate measurement in μm per μsec can be converted to m per sec. Similar velocity measurements can be performed for each nozzle by mouse clicking on the various nozzles. Other versions of the scale can also be implemented in the Tools menu button.

Figure 9:
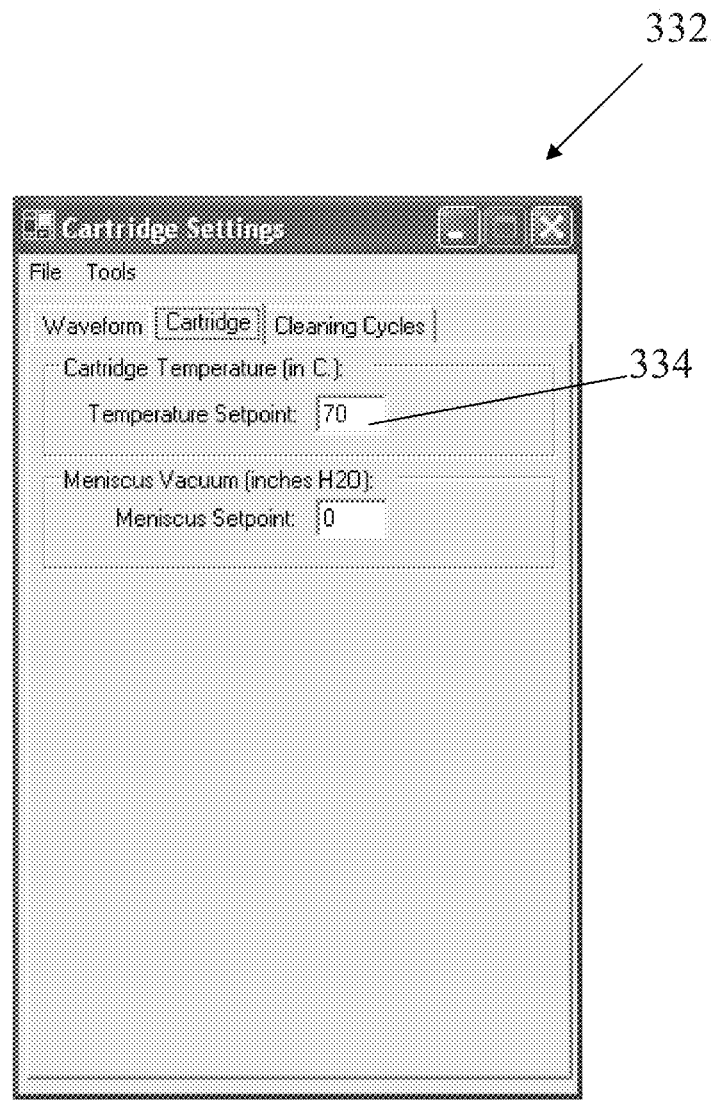
FIG. 9 is a representative screenshot of a Cartridge Settings interface.

Referring back to FIG. 5, a user selection of the next GUI tab, "Cartridge," 330 launches a Cartridge Settings interface 332 (FIG. 9). As described above, if a viscosity of a fluid in the cartridge is too high, the interface can be implemented to adjust the cartridge temperature to a higher level by allowing the user to enter a desired temperature in the cartridge temperature input box 334. An increase in the cartridge temperature effectively increases the temperature of the fluid in the cartridge and decreases the viscosity of the fluid.

Figure 10:
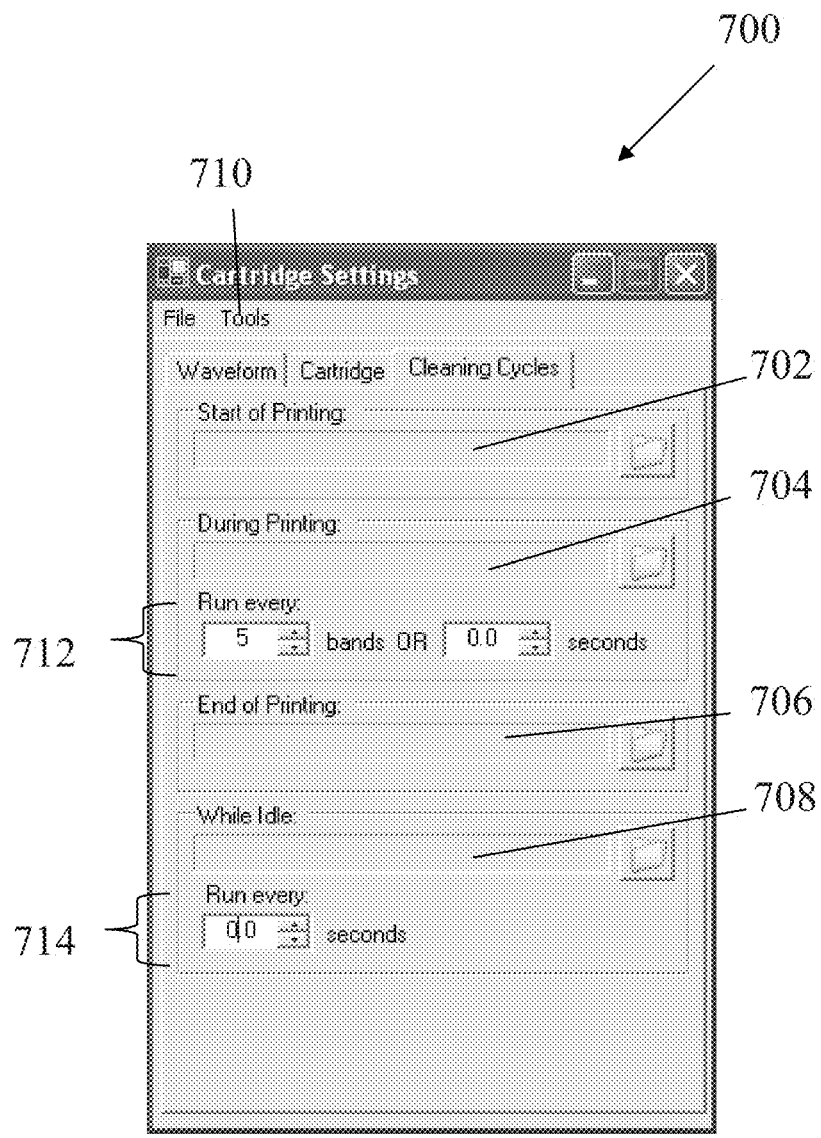
FIG. 10 is a representative screenshot of a Cleaning Cycles interface.
Figure 11:
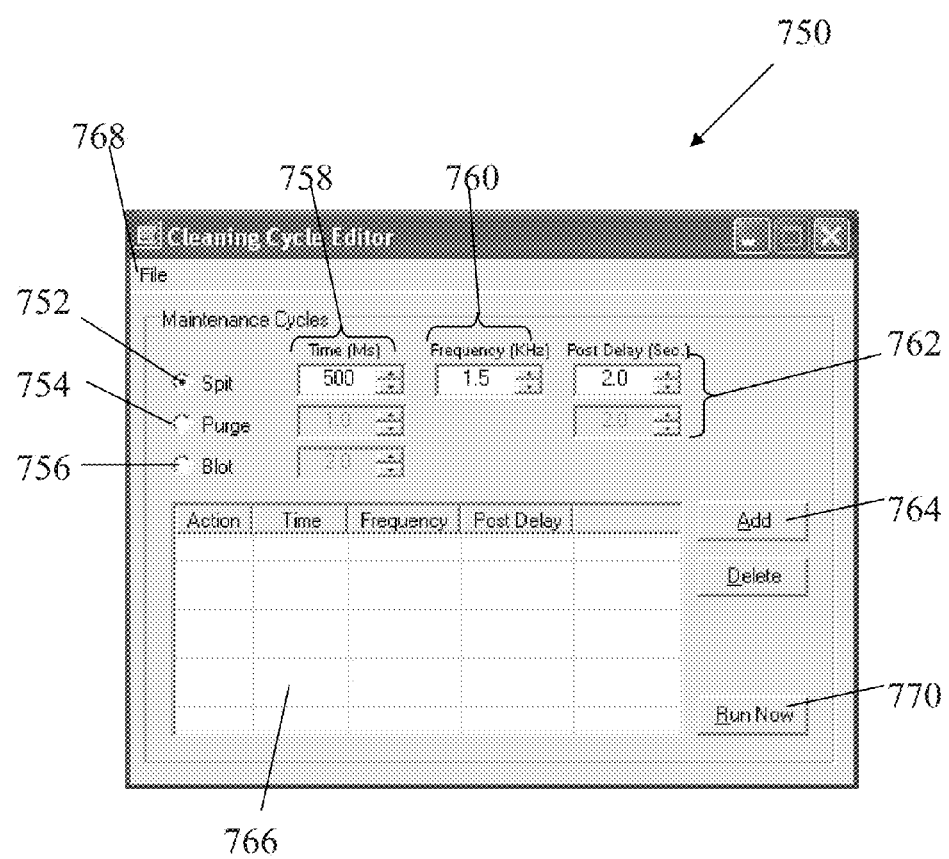
FIG. 11 is a representative screenshot of a Cleaning Cycle Editor.

User selection of a "Cleaning Cycles" tab 350 can launch a Cleaning Cycles Interface 700 (FIG. 10) to allow the user to set cartridge maintenance profiles for printing. The user can selected a predetermined Cleaning Cycle to run at the Start of Printing 702, During Printing 704, End of Printing 706, and While Printing 708 using the corresponding file select windows. In addition, the user can select frequency (712 and 714) of the clean cycle running During Printing and While Idle. Some fluids do not need maintenance while others need a high amount of maintenance to keep the nozzles clear and functioning properly. Keeping the nozzles clear can include pushing the fluid through the nozzles to remove air bubbles. FIG. 11 represents a Cleaning Cycle Editor 750 for editing existing cleaning cycle parameters and creating new cleaning cycles. The user can launch the Cleaning Cycle Editor through the Tools menu button 710. A cleaning cycle can be very simple such as a "2 second Blot" where the carriage simply goes to the cleaning station and "Blots" the cartridge with the cleaning pad. The cleaning cycle can also be several actions long. To create a Cleaning Cycle, the user can click on the "Spit" 752, "Purge" 754, or "Blot" 756 buttons. Then the user can enter a number or use the arrows for the 'Time" 758, Frequency" 760 or "Post Delay" 762 input boxes. Clicking on the "Add" button 764 will enter the clean cycle into a table 766. The user created Cleaning Cycle can be saved by selecting the "File" menu button 768. Appropriate file name describing the parameters should be given for each stored Cleaning Cycle, to facilitate identification at a future time. A mouse click of the "Run Now" button 770 executes the selected Clean Cycle.

Figure 12:
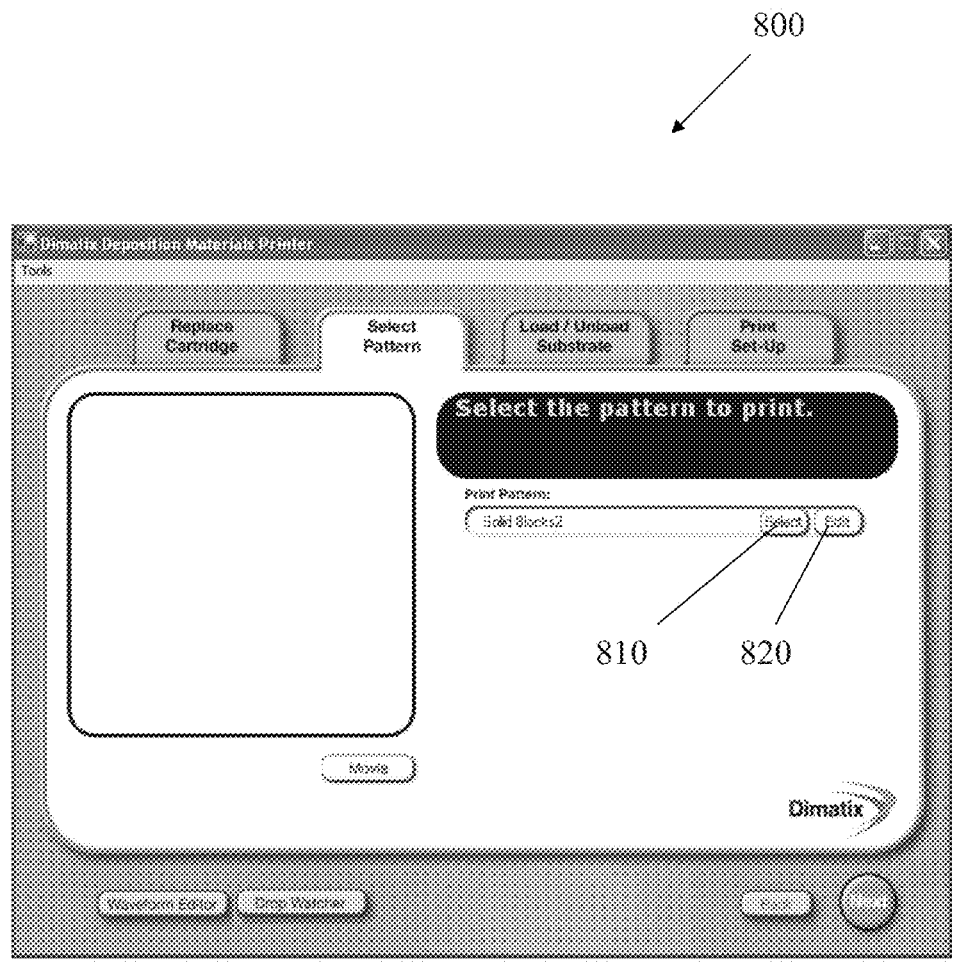
FIG. 12 is a representative screenshot of a Select Pattern interface.
Figure 13:
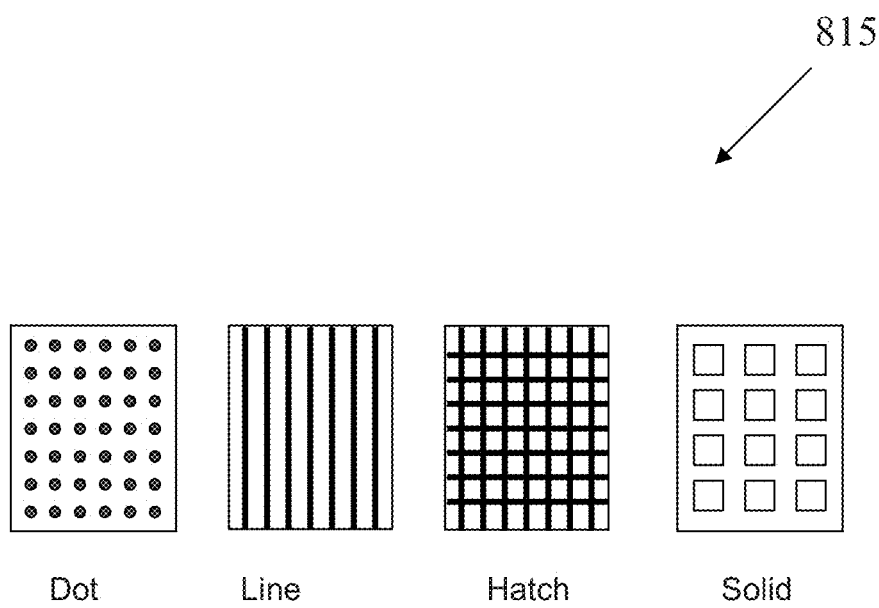
FIG. 13 represents some of the Predetermined Print Patterns stored in a file.
Figure 14:
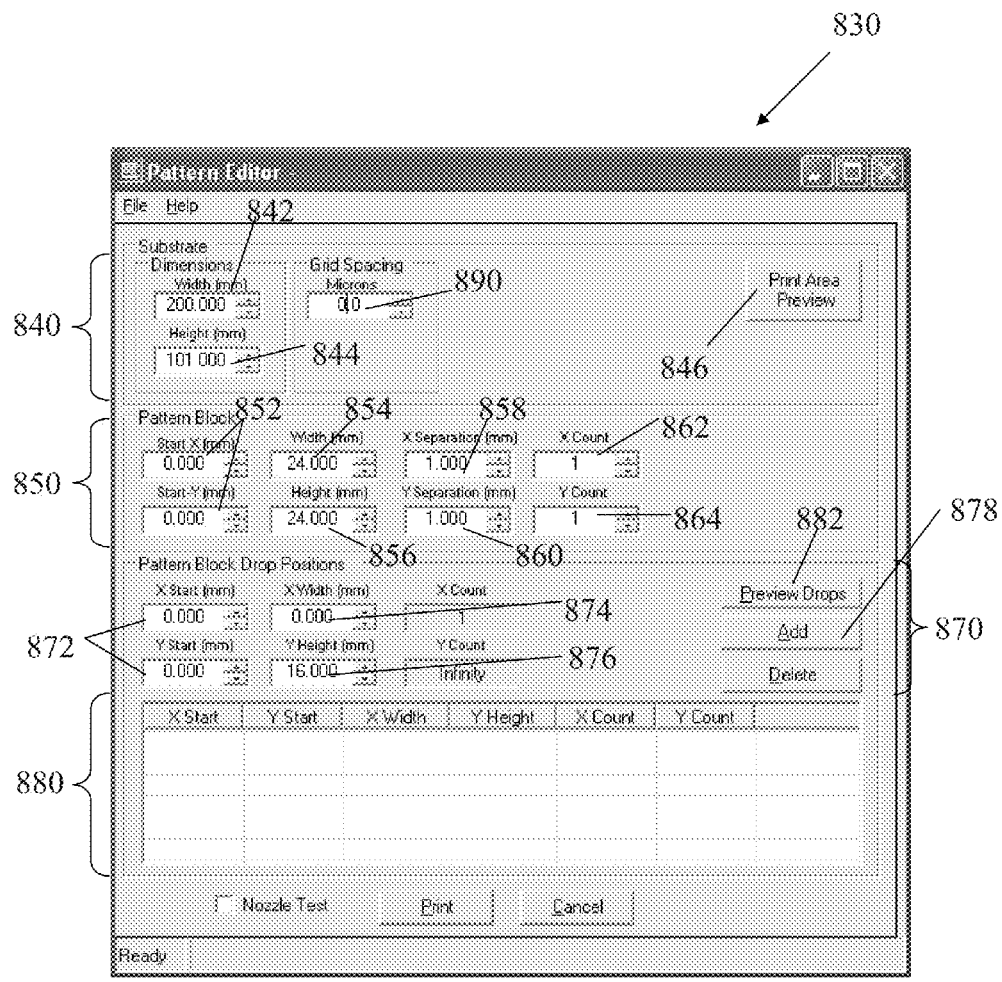
FIG. 14 is a representative screenshot of a Pattern Editor.
Figure 15:
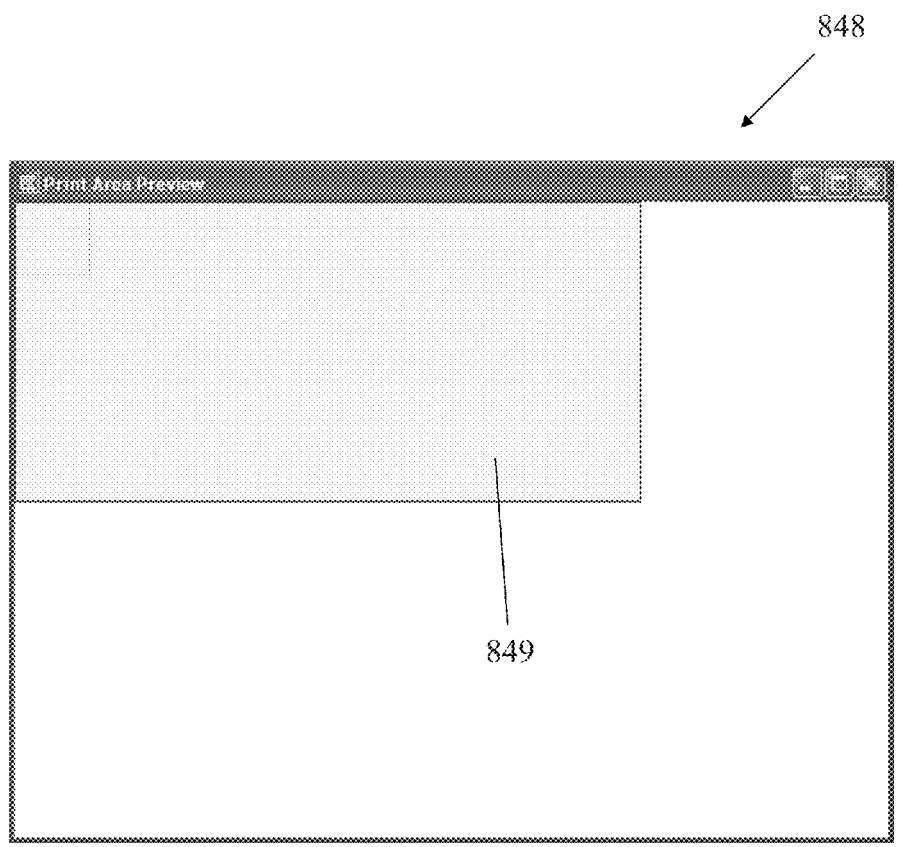
FIG. 15 is a representative screenshot of a Print Area Preview screen.

Referring back to FIG. 5, the Select Pattern tab 220 can be selected by a mouse click to activate a Select Pattern Interface 800 for creating new print patterns or editing existing print patterns. FIG. 12 displays a screenshot of the Select pattern Interface 800 comprising a "Select" button 810 for selecting predetermined print patterned stored in a file and a "Edit" button 820 for editing a predetermined print pattern or creating a new print pattern. FIG. 13 is a representative list of possible predetermined print patterns 815. The user can create a new print pattern by mouse clicking on the Edit button 820 and activating the Pattern Editor 830 (FIG. 14). The Substrate edit area 840 can allow the user to edit the "Dimensions" or the total print area by entering a value into a Width box 842 and a Height box 844. Generally jetting is performed on only a single substrate, but a user could place several smaller substrates on the platen and jet on them at once. For example, when jetting biological fluids such as DNA, the substrate could be a collection of multiple wells for jetting small volume of DNA into each well to conduct multiple reaction processes. The user can mouse click on a Print Area Preview button 846 to launch a pop up window 848 (FIG. 15) showing the user designated area. The total area of the window represents the platen 102. If the substrate is smaller than the platen it will show as a beige shape Substrate area 849 inside a white area. The user can then make the necessary adjustments based on the displayed print area.

Located below the Substrate edit area 840 can be a Pattern Block Edit area 850, which allows the user to specify a Pattern Block area delineated within the Substrate area. In the Pattern Block edit area 850, the user can enter a starting point of a pattern area in X-Y coordinates 852. A Width 854 and Length 856 can also be specified to designate the total area of the pattern. Multiples of the same pattern in the user designated print area can be printed by entering a spacing between each pattern in X-Separation 858 and Y-Separation 860 boxes, and the number of patterns to print in the horizontal direction (X Count 862) and in the vertical direction (Y Count 864). The DNA jetting application describe above could also be applicable here.

Figure 16:
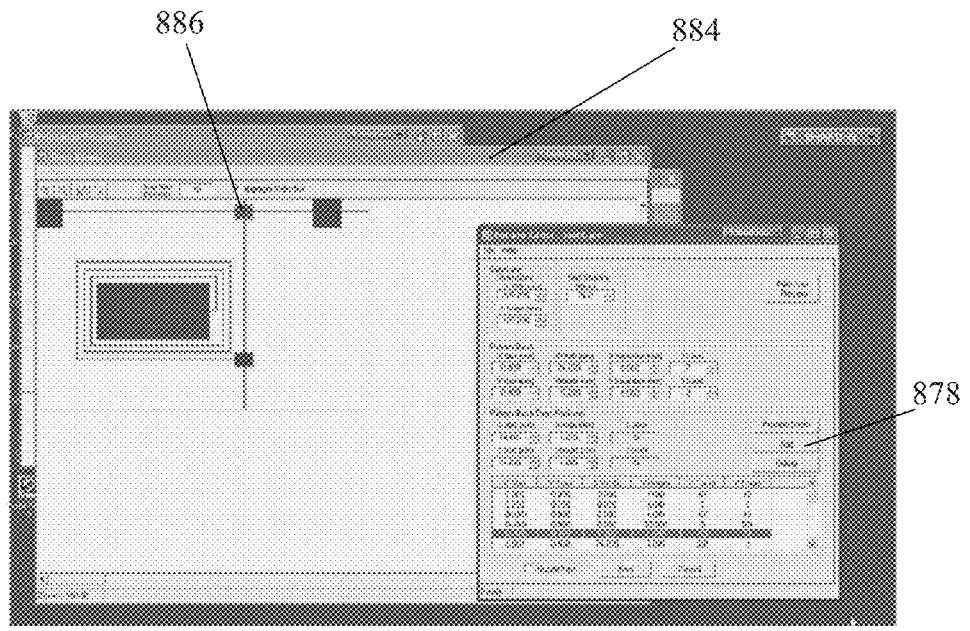
FIG. 16 is a representative screenshot of a Preview Drops screen.

The third Pattern Editing area can be a Pattern Block Drop Position area 870 to designate a starting point of the pattern and features of the pattern. In the Pattern Block Drop Position area 870, the user can enter the position in X-Y coordinates 872 of a first fluid drop location in the Pattern. The user can also enter a Width 874 and Height 876 of a feature of the pattern. For a 10 mm horizontal line having a thickness of 200 microns, the user can enter the length in the x direction (X Width=10 mm) and the width in the y direction (Y Height=200 microns). For the same vertical line, X Width=200 micron X and Y Height=10 mm. Thus the pattern generated can be in rectangles of X width and Y height. The user can enter the dimensions for the feature in the appropriate boxes and mouse click on the Add button 878 to placed them in a Table 880. The user can mouse click on a Preview Drops button 882 to launch a pop up window 884 (FIG. 16) to display the designated pattern. The user can click on a line of data in the Table 880 specifying a feature, and that feature will show up as red spot 886 on the Preview drops window 884. The user can Zoom in and out on the feature to see the individual spots. The user can also highlight a line in the Table 880 and mouse click on a Add button 878 to duplicate that feature. The duplicated feature will be jetted right on top of the original feature unless the X-Y start coordinates 872 are adjusted in the appropriate boxes. Referring back to the Substrate edit area 840, a Grid Spacing 890 is the X-Y distance between the drops jetted to create a pattern. For example, with a 50 micron Grid Spacing, the drops will be jetted 50 microns apart in X and 50 microns apart in Y to create the pattern. So, for a 100 micron wide, 10 mm tall vertical line, the system will place 3 drops in the X direction (one for the first edge, another at 50 micron, and another at 100 microns for the next edge) by 2,000 tall.

Figure 17:
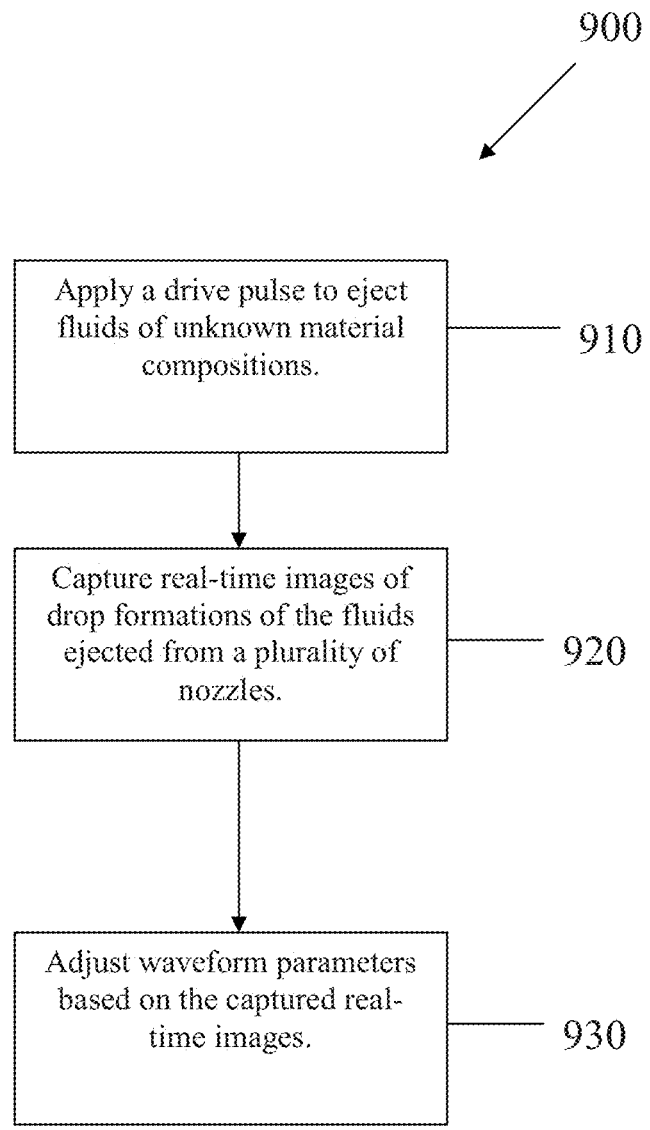
FIG. 17 is a flowchart of a method of performing real-time waveform editing.

FIG. 17 is a flow diagram summarizing a method of facilitating adjustments to the waveform parameters. In the first step 910, a drive pulse is applied to the plurality of nozzles. The amplitude of the drive pulse should be sufficiently large to effect fluid drop ejection. In the second step 920, the drop watcher camera system captures real-time images of the drop formations of the fluid from user selected nozzles. Depending on the elemental composition and drop formations and characteristics, one or more of the waveform parameters need to be adjusted to optimize fluid drop ejection. In the third step 930, the user reviews the real-time images of fluid drops ejected from the nozzles and adjusts appropriate waveform parameters.

A number of references to functions that can be executed to by the processor 101 are described above. It should be understood that more than one processor can be used, and reference to processor 101 is exemplary. Additionally, in one implementation, a user input device can be mounted directly onto the fluid deposition device 100, for example, as a touch pad and/or screen. Other forms of user input devices can also be used.

Embodiments of the subject matter and the functional operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer program products, i.e., one or more modules of computer program instructions encoded on a tangible program carrier for execution by, or to control the operation of, data processing apparatus. The tangible program carrier can be a propagated signal or a computer readable medium. The propagated signal is an artificially generated signal, e.g., a machine-generated electrical, optical, or electromagnetic signal, that is generated to encode information for transmission to suitable receiver apparatus for execution by a computer. The computer readable medium can be a machine-readable storage device, a machine-readable storage substrate, a memory device, a composition of matter effecting a machine-readable propagated signal, or a combination of one or more of them.

The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, or declarative or procedural languages, and it can be deployed in any form, including as a stand alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, to name just a few.

Computer readable media suitable for storing computer program instructions and data include all forms of non volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, input from the user can be received in any form, including acoustic, speech, or tactile input.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described is this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

While this specification contains many specifics, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

A number of embodiments have been described. Other embodiments are within the scope of the following claims.

What is claimed is:

1. A system comprising:
   a computer system configured to control a deposition system comprising a plurality of nozzles including a first nozzle;
   a graphical user interface to the computer system, the graphical user interface configured to control waveform parameters for jetting a fluid through the first nozzle, the waveform parameters depending on the fluid to be jetted;
   a camera coupled to the lab deposition system, the camera configured to provide real-time feedback information of a fluid ejected through the first nozzle, the graphical user interface configured to allow a user to adjust waveform parameters of a drive pulse delivered to the first nozzle based on the real-time feedback information; and
   a drop watcher communicatively coupled to the camera and a waveform editor, the drop watcher configured to display real-time still images and video images of the fluid jetting through the first nozzle.

2. The system of claim 1, wherein the graphical user interface further comprises the waveform editor, and the waveform editor is configured to adjust the waveform parameters for the fluid.

3. The system of claim 2, wherein the waveform parameters comprise at least a parameter selected from the group consisting of a voltage level, a slew rate, a duration, a plurality of segments, a frequency, and a width of the drive pulse delivered to the first nozzle.

4. The system of claim 3, wherein the waveform editor is configured to adjust the voltage level of the drive pulse in step-wise increments.

5. The system of claim 2, wherein the drive pulse comprises a jetting waveform and a non-jetting waveform.

6. The system of claim 5, wherein the waveform editor is further configured to adjust the non-jetting waveform by applying a low amplitude pulse to the first nozzle to move a meniscus of a fluid drop of the fluid without ejecting the fluid drop.

7. The system of claim 2, wherein the waveform editor is further configured to adjust the waveform parameters to add or subtract waveform segments.

8. The system of claim 2, wherein the graphical user interface is further configured to provide the waveform editor and the drop watcher simultaneously to a user.

9. The system of claim 2, further comprising a storage unit communicatively coupled to the computer system, the storage unit configured to store a plurality of predetermined drive pulses, wherein the waveform editor is configured to select one of the stored predetermined drive pulses.

10. The system of claim 9, wherein the waveform editor is configured to select the predetermined drive pulse based on the fluid to be jetted.

11. The system of claim 1, wherein the fluid comprises a material used to manufacture a display.

12. The system of claim 1, wherein the fluid comprises a metal.

13. The system of claim 1, wherein the fluid comprises an ink.

14. The system of claim 1, wherein the fluid comprises an organic material.

15. The system of claim 1, wherein the fluid comprises a biological material.

16. A method of operating a system comprising a plurality of nozzles, the method comprising:
    applying a first drive pulse to a nozzle to eject a fluid through a nozzle;
    capturing a real-time visual feedback information of the fluid being ejected through the nozzle; and
    adjusting a plurality of waveform parameters based on the captured visual feedback information to establish a second drive pulse which can be used to eject further fluid through the nozzle, and
    providing a graphical user interface on a computer system, wherein the graphical user interface is configured to control the waveform parameters, wherein adjusting the plurality of waveform parameters comprises reducing a voltage for the second drive pulse relative to a voltage of the first drive pulse.

17. The method of claim 16, further comprising applying the second drive pulse to the nozzle to eject fluid through the nozzle.

18. The method of claim 16, wherein capturing the real-time visual feedback information comprises capturing still images and video images of the fluid jetting through the nozzle.

19. The method of claim 16, wherein adjusting the waveform parameters further comprises adjusting at least one parameter selected from the group consisting of a slew rate, a duration, a plurality of segments, a frequency, and a width of the drive pulse applied to the nozzle.

20. The method of claim 16, wherein adjusting the waveform parameters comprises adjusting a voltage level in stepwise increments.

21. The method of claim 16, wherein the waveform comprises a jetting waveform and a non-jetting waveform.

22. The method of claim 21, further comprising adjusting the waveform parameters of the non-jetting waveform by applying a low amplitude pulse to the nozzle to move a meniscus of a fluid drop of the fluid without ejecting the fluid drop.

23. The method of claim 16, wherein adjusting the waveform parameters further comprises adding or subtracting waveform segments to the drive pulse.

* * * * *

UNITED STATES PATENT AND TRADEMARK OFFICE
CERTIFICATE OF CORRECTION

PATENT NO. : 9,195,237 B2  
APPLICATION NO. : 14/269403  
DATED : November 24, 2015  
INVENTOR(S) : Deane A. Gardner et al.

Page 1 of 1

It is certified that error appears in the above-identified patent and that said Letters Patent is hereby corrected as shown below:

In the Claims

Column 12, line 64, in Claim 16, delete "nozzle," and insert -- nozzle; --, therefor.

Signed and Sealed this
Twenty-sixth Day of April, 2016

Michelle K. Lee
*Director of the United States Patent and Trademark Office*